United States Patent

Wagner et al.

[11] Patent Number: 5,961,470
[45] Date of Patent: Oct. 5, 1999

[54] BREATH TEST FOR ASSESSING HEPATIC FUNCTION

[76] Inventors: David A. Wagner, 23 Thoreau Dr., Hillesboro County, Nashua, N.H. 03062; Graham M. Woolf, 2170 Century Park East, Apartment 1607, Los Angeles County, Los Angeles, Calif. 90067

[21] Appl. No.: 08/890,570

[22] Filed: Jul. 9, 1997

[51] Int. Cl.[6] ............................... A61B 5/08; A61B 6/00
[52] U.S. Cl. ..................... 600/532; 600/543; 424/9.1; 435/810; 436/34; 436/811; 436/900; 436/86
[58] Field of Search ...................... 128/200.24; 424/1.81, 424/9.1; 436/57, 900, 34, 811, 86; 73/23.3; 600/532, 529, 531, 543, 301; 435/810

[56] References Cited

U.S. PATENT DOCUMENTS

| | | | |
|---|---|---|---|
| 4,830,010 | 5/1989 | Marshall | 600/532 |
| 5,100,779 | 3/1992 | Watkins | 435/25 |
| 5,112,827 | 5/1992 | Saunders et al. | 514/263 |
| 5,262,156 | 11/1993 | Alemohammad | 424/92 |
| 5,290,678 | 3/1994 | Jackowski | 435/7.4 |
| 5,428,063 | 6/1995 | Barak et al. | 514/556 |
| 5,654,404 | 8/1997 | Roos et al. | 530/387.3 |

OTHER PUBLICATIONS

V.R. Young, et. al. Am J. Clin. Nutr. 54:386–94, 1991.
K.J. Storch, et al. Am. J. Clin. Nutr. 54:377–85, 1991.
A. Andersson, et al. Clin. Chim. Acta 192:69–76, 1990.
Kubota et al., J. Nucl. Med. 32:2118–23, 1991.
E. Hayama, et al. Eur. J. Drug Metab. Pharmocokinet 16:287–97.
Blom et al., Hepatology 13:445–54, 1991, Kaye et al., Drugs 340:124–8, 1990.
Martensson, et al., Scand. J. Gastroentrol. 27–405–11, 1992.
Gastorenterology vol. 88, p. 1678.
Lauterburg et al., Hepatology 17:418–422, 1993.
S. Leskinen–Kallio, et al. Dept. of Oncology and Radiotherapy, Nuclear Medicine and Turku Medical Cyclotron–PET Center.

*Primary Examiner*—Kimberly L. Asher
*Attorney, Agent, or Firm*—Jenkens & Gilchrist, A Professional Corporation

[57] ABSTRACT

Provided herein is a novel breath test for assessing hepatic function. The test involves administration of a labeled methionine or methionine metabolite to a subject and measurement of the expired label.

24 Claims, 3 Drawing Sheets

Figure 1: $^{13}$C-Methionine Metabolism

Figure 2: MBT Test 1 vs Test 2 data for controls and liver patients.

Figure 3: Relationship between the MBT and CP classification in alcoholic and non-alcoholic liver patients.

BREATH TEST FOR ASSESSING HEPATIC FUNCTION

BACKGROUND OF THE INVENTION

1. Field of the Invention

The present invention relates to a method for monitoring hepatic disease or dysfunction. More specifically, the invention relates to administering labeled methionine or methionine metabolites to an individual and assessing expired labeled carbon dioxide.

2. Description of the Prior Art

Standard serologic and biochemical serum liver tests have been used to determine the presence of liver disease. However, these tests do not provide an accurate assessment of hepatic functional capacity nor do they detect changes in hepatic disease severity (Gitnick, G. *Surg. Clin. N. Am.* 61:197–207 [1981]). Increasing prothrombin time and decreasing serum albumin concentrations have been used as prognostic indicators of progressive liver disease (Rydning, A., et al. *Scand. J. Gastroenterol.* 25:119–126 [1990]). Significant changes in prothrombin time and albumin may occur in patients for reasons other than liver dysfunction and, at times, only after severe liver decompensation. Further, radiological testing and histological examination of liver biopsies are poor indicators of decreasing hepatic function.

The Child-Pugh (CP) classification is used to determine the degree of liver disease severity. The CP classification reflects the sum of scores derived from clinical and laboratory parameters. Disadvantages of the CP classification include subjective measures (degree of ascites and encephalopathy) and dependence on serum tests (bilirubin, albumin, and prothrombin time) that may be influenced by extrahepatic factors. As a result, the CP classification is a poor measure of patient status and is insensitive to small changes in the patient's condition.

During the last twenty years, much work has been devoted to devising quantitative liver tests. Liver function can be subdivided into three compartments: 1) cytosolic, 2) microsomal, and 3) mitochondrial. Each compartment's function can be evaluated with both quantitative serum and breath tests.

Blood and breath tests have been used for assessing mitochondrial-compartment hepatic function. A typical blood test is the measurement of the arterial ketone body ratio (AKBR). The hepatic mitochondrial redux potential ratio (ratio of NAD/NADH) correlates with the ketone body ratio (acetoacetate/β-hydroxy butyrate) in liver disease. Serial changes in the AKBR can predict hepatic dysfunction, postoperative graft viability, and acute rejection (Asonuma K., S., et al. *Transplantation.* 51:164–171 [1991], Mori K, K., et al. *Ann. Surg.* 211:438–446 [1990]) post liver transplantation. However, recent experiments by Matsushita et al. determined that extrahepatic metabolism of ketone bodies diminishes the value of the AKBR (Matsushita K. et al. *Hepatology.* 20:331–335 [1994]). Additional disadvantages of the AKBR are its labor-intensiveness and the requirement for arterial blood.

Breath tests can also be used to access the mitochondrial compartment hepatic function. The first substrate used as a breath test to measure mitochondrial function was the keto-analog of leucine ketoisocaproic acid (KICA) (Michaletz P. A., et al. *Hepatology.* 10:829–832 [1989]). Decarboxylation of KICA occurs mainly in hepatic mitochondria since anhepatic animals have a 75% reduction in $^{14}CO_2$ production. Alcohol, which is known to alter the NAD/NADH ratio, deceases KICA decarboxylation. Further experiments with sodium salicylate, an uncoupler of mitochondrial respiration, showed an increase in KICA decarboxylation.

The $^{13}C$ and $^{14}C$-KICA breath tests have been used to access mitochondrial function in controls and in patients with alcoholic and non-alcoholic liver disease (Lauterburg B H, et al. *Hepatology* 17:418–422 [1993]). The KICA breath test showed impaired mitochondrial function in the alcoholic patients compared to controls and non-alcoholic patients. Patients with alcoholic disease had normal aminopyrine breath test and galactose elimination capacity (both measurements of cytosolic function) despite decreased mitochondrial function. These results suggest that KICA decarboxylation reflects hepatic mitochondrial function in patients with chronic alcoholic liver disease.

The $^{13}C$-KICA breath test has also been used to differentiate between alcoholic and nonalcoholic liver-diseased patients (Witschi, A., et al. *Alcohol Clin. Exp. Res.* 18:951–955 [1994], Mion F, et al. *Metabolism.* 44:699–700 [1995]). Lauterburg and co-workers have shown that the $^{13}C$-KICA test can detect mitochondrial changes with the ingestion of the equivalent of two alcoholic drinks or with therapeutic doses of acetylsalicylic acid (ASA, aspirin) (Lauterburg B H, et al. *J. Lab. Clin. Med.* 125:378–383 [1995]). However, the KICA breath test is not widely used. Disadvantages of the KICA breath test are the high cost of the stable isotope and its instability in solution.

These and other disadvantages of the prior art are overcome by the present invention. As shown herein, we provide a novel breath test for assessing hepatic disease or dysfunction.

SUMMARY OF THE INVENTION

The present invention overcomes the limitations of the prior art and provides a method and kit for the assessment of mitochondrial-compartment hepatic function.

Provided herein is a method of assessing hepatic mitochondrial function in a subject comprising the steps of: a) administering to said subject an effective amount of carbon-labeled methionine or carbon-labeled methionine metabolite to said subject; b) collecting expired breath from said subject; and c) measuring the amount of label in said expired breath to assess hepatic mitochondrial function in said subject. The label is a carbon label. Preferably the labeled compound administered is $^{13}C$ methionine or $^{13}C$ methionine metabolite, or mixtures thereof. The labeled methionine metabolite is selected from the group consisting of carbon-labeled S-adenosylmethionine, S-adenosylhomocysteine, homocysteine, cystathionine, homoserine and α-ketobutyrate. The carbon-labeled compound may comprise a plurality of labeled carbons.

The method further comprises comparing said amount of expired labeled carbon with a standard, whereby said comparing yields a measure of hepatic mitochondrial function. The standard comprises the mean value of expired label in a control population without hepatic disease or hepatic dysfunction.

The hepatic disease or dysfunction that may be assessed with this method or kit includes liver disease or dysfunction associated with an impairment in the mitochondrial compartment of hepatic tissues. The disease or dysfunction is selected from the group consisting of chronic liver disease, fulminant hepatic failure, viral-induced liver disease, metabolic liver disease, and hepatic dysfunction associated with sepsis or liver trauma.

The label may be measured by techniques commonly used for measuring the presence of labeled species. Isotopic measurement of label is selected from the group consisting of mass spectrometric measurement, laser measurement, infrared detection, nuclear magnetic resonance and liquid scintillation counting of labeled carbon.

The present invention also provides a kit for assessing hepatic mitochondrial function comprising carbon-labeled methionine or carbon-labeled methionine metabolite in a pharmaceutically acceptable carrier, and a means for collecting expired breath.

The advantages of the present invention may be gleaned from the following detailed description.

DETAILED DESCRIPTION OF THE INVENTION

Figure 1:
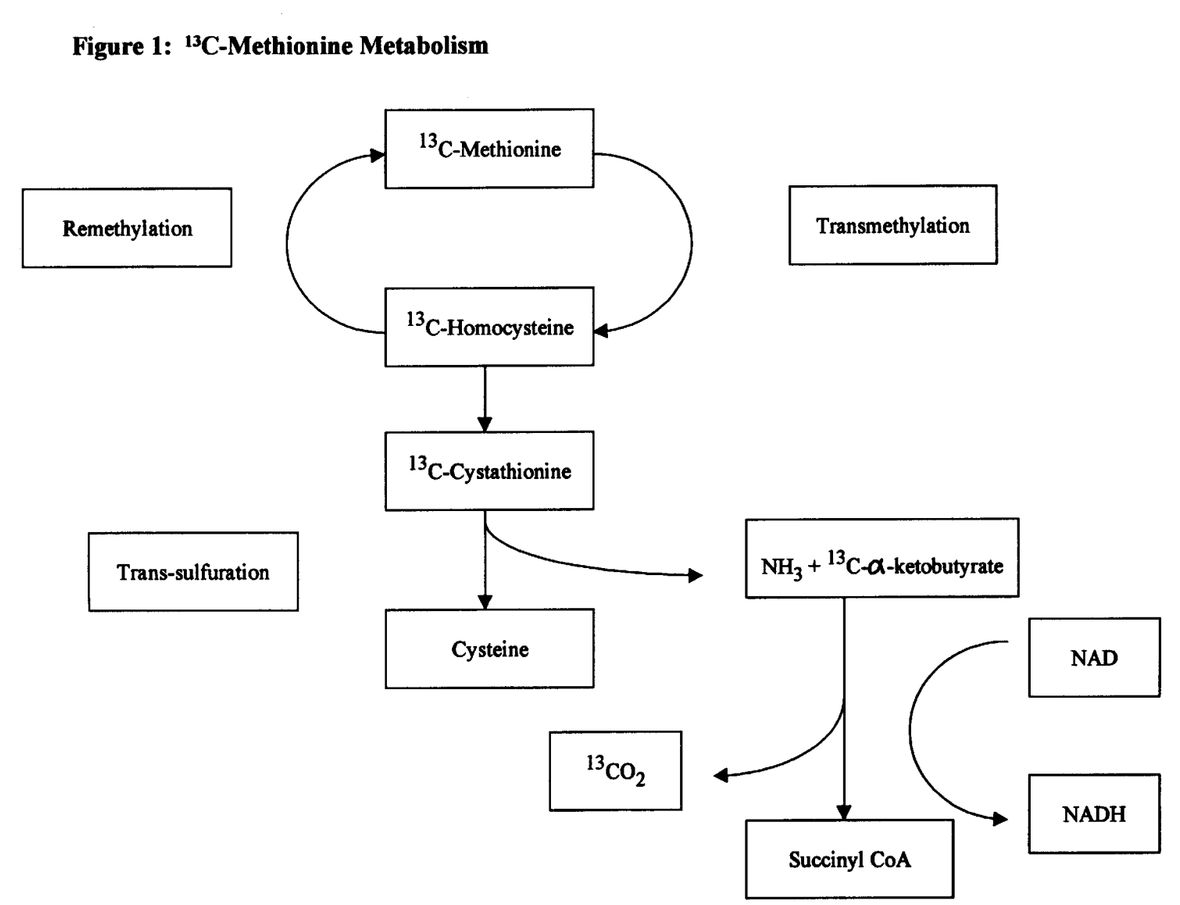
FIG. 1: Metabolism of methionine.

Methionine is an essential amino acid which has important roles in various metabolic processes, including protein synthesis (Lehninger, A. L. "Biochemistry." 1977 Worth Publishers, Inc. New York., Storch, K. J., et al. *Am.J. Physiol.* 255:E322–E331 [1988]). $^{13}$C-Methionine is metabolized via a transsulfuration pathway to cystathionine which is subsequently metabolized to alpha-ketobutyrate. Metabolism of alpha-ketobutyrate occurs solely in the hepatic mitochondria with release of $^{13}CO_2$ and reduction of NAD to NADH. These reactions are illustrated in FIG. 1.

Methionine metabolism is impaired in liver disease. Fasting levels of plasma methionine are elevated and the intravenous plasma clearance of methionine is reduced in liver disease when compared to healthy controls (Kinsell, L. W., et al. *Science.* 106:589–590 [1947]; Clowes, G. H. A. J., et al. *Surgery.* 96:675–684 [1984]; Horowitz JH, et al. *Gastroenterology.* 81:668–675 [1981]; Marchesini G, et al. *Hepatology.* 16:149–155 [1992]). Urinary sulfate excretion was also significantly decreased in cirrhotic patients. This suggests that a block in the transsulfuration pathway occurs with liver disease. Methionine plasma clearance was reduced in cirrhotic patients compared with controls. Methionine clearance correlated with the GEC (r=0.82) and with the CP score (r=-0.80). The reduced metabolism of methionine and the decreased formation of methionine end products indicate that mitochondrial function is impaired in cirrhotics.

The present invention features a method of determining hepatic function in a patient using a breath test. This breath test is sufficiently sensitive to allow detection of not just chronic hepatic conditions where the liver is already irreparably damaged but it also is able to uncover these conditions at an early stage because of its dynamic nature.

The method of the invention commences with a step of administering, preferably orally, a dose of a carbon-labeled methionine to a subject. In an additional embodiment, a carbon-labeled methionine metabolite may be administered to the subject. Useful methionine metabolites include compounds which are transported across the mitochondrial membrane into the mitochondria. Useful metabolites include, but are not limited to metabolites selected from the group consisting of S-adenosylmethionine, S-adenosylhomocysteine, homocysteine, cystathionine, homoserine and α-ketobutyrate, and mixtures thereof. As used herein, the term "compound" refers to labeled methionine or methionine metabolite. Oral administration ensures that the liver, rather than some other organ, gets the first chance to metabolize the labeled compound. The compound is oxidized in the patient, the expired breath from the patient is collected, and the amount of isotope in the expired breath is analyzed. The amount of expired isotope determined is compared with the standard and this comparison yields a measure of hepatic function. If the compound is administered orally, it preferably is in a pharmaceutically acceptable carrier such as water or a sugar solution but may be delivered chemically bound as a peptide or similar entity and released upon digestion. Alternatively, it may be administered intravenously.

The preferred labeled isotope is a carbon isotope which yields expired carbon dioxide. The preferred carbon isotopes are $^{13}$C and $^{14}$C. $^{13}$C is more preferred because it is a stable rather than a radioactive isotope.

Methionine or methionine metabolite having an isotope label at the 1-carbon position are preferred. This is because the 1-carbon is excised and exhaled as carbon dioxide at an early step in the oxidative process. However, in an alternative embodiment of the present invention, the compound may have a plurality of carbons labeled. If a $^{13}$C isotope is used, the preferred method of measurement is with a mass spectrometer, but other detection methods can be used, as would be known to one skilled in the art. These include, but are not limited to laser measurement, infrared detection, nuclear magnetic resonance and liquid scintillation counting of labeled carbon.

The method of the invention can be used to detect hepatic dysfunction and disease by comparing a standard in the form of the mean value of expired isotope in a normal population with value determined from the test subject. This test can be used in identifying the presence of liver dysfunction caused by chronic liver diseases, fulminant hepatic failure, metabolic liver diseases, and liver dysfunction seen in septic or injured patients. For a further and more detailed description of these states, see *Hepatology Textbook of Liver Disease*, Zakim and Bayer, (W. B. Saunders 1990), incorporated by reference herein.

The present invention features a breath test for determining problems in hepatic function. This test is a dynamic rather than a static test and shows hepatic function rather than merely liver cell degradation. The test is relatively inexpensive to carry out and yields rapid results. While radioactive isotopes can be used in the test, it preferably is carried out with stable isotopes.

In the preferred embodiment, the individual is first required to fast overnight. This minimizes metabolic effects of meal absorption and the contribution of endogenous label appearing in the breath from natural levels of the endogenous isotope in the diet. However, the test may be conducted without requiring overnight fasting. Preferably at least two baseline breath samples are collected and the mean isotope value in these samples is used as a background. In an alternative embodiment, only one background measurement is made or, alternatively, no background measurement is made. If no background measurement is made, the amount of label in the expired breath is taken as the measurement for comparison with a control value. If a background measurement is made, this background is subtracted from the labeled carbon levels determined following isotopic administration in order to obtain the change in labeled species level.

If the compound is administered orally, it is preferable to wait a sufficient amount of time after administration before collecting the breath sample(s) to allow metabolism of the labeled compound to release the labeled species. A sufficient amount of time is about 5 minutes to about 120 minutes, preferably about 10 minutes to about 90 minutes, and most preferably about 30 minutes to about 60 minutes. If the compound is administered intravenously, the sufficient amount of time is about 5 minutes to about 120 minutes, preferably about 10 minutes to about 90 minutes, and most preferably about 30 minutes to about 60 minutes.

If the compound is an amino acid or methionine metabolite with a chiral center, it is preferably the L-stereoisomer, but may also be the D-stereoisomer or a racemic mixture thereof.

All breath samples, both those collected prior to administration of the isotope and those after administration, may be collected with a commercially available breath sampler. These include, but are not limited to a Quintron AlveoSampler (Milwaukee, Wis.). These samplers have a mouthpiece and a collection bag with a one-way valve there between. The breath samples are trapped in a collection bag or other suitable breath collection device and the contents are injected into an evacuated tube such as, but not limited to an Exetainer tube (Labco Ltd, U.K.).

The following examples serve to illustrate specific embodiments of the invention, but should not be considered as a limitation on the scope of the invention.

EXAMPLE 1

Reproducibility of the MBT (ethionine Breath Test) in Healthy Controls

The objective of this study was to conduct the MBT twice within 7 days in 20 healthy controls. This information provides the inter and intra-subject reproducibility of the MBT. The study included 20 healthy volunteers (11 females and 9 males) with a mean age of 33 years (range 18–59). Females were not pregnant or lactating. Patients were not allowed to ingest alcohol, ASA or caffeine and did not smoke 12 hours prior to the test. The MBT was performed while participants were at rest and after an 8 hour fast. Duplicate baseline breath samples were taken before administering the methionine dose. Controls exhaled normally into a 3 liter Quintron (Milwaukee, Wis.) breath collection bag. A breath sample was obtained through a sampling port and stored in a 10 cc Exetainer tube (Labco, Ltd., U.K.).

A pre-measured 100 mg dose of L-1-$^{13}$C-methionine (MassTracer, Woburn, Mass.) was solubilized in 20 ml sterile water and administered orally. The cup was immediately filled with an additional 150–200 ml of water and consumed by the patient. Following the administration of the dose, duplicate breath samples were collected at 10, 20, 30, 40, 50, and 60 minutes. The amount of $^{13}CO_2$ in the Exetainer breath storage tubes was measured with a Europa Scientific 20/20 gas isotope ratio mass spectrometer (Europa Scientific, Cincinnati, Ohio). The ratio of $^{13}CO_2$ to $^{12}CO_2$ (mass 45 to 44) is measured in the sample and compared to a reference gas (5% $CO_2$, balance 75% $N_2$, 20% $O_2$). The reference gas has been calibrated against international standards. The units of measurement are atom % $^{13}$C and defined by:

$$\text{Atom \% } ^{13}C = {}^{13}CO_2/({}^{13}CO_2 + {}^{12}CO_2) \times 100\%$$

$CO_2$ standards at three different enrichments, covering a range similar to that produced by a typical breath test, are run before and after each daily run to check instrument performance. The analytical precision of the instrument is 0.0001 atom % $^{13}$C.

The atom percent excess (APE) $^{13}$C values for each 10 minute breath sample interval were determined for a one hour period. We used the peak enrichment (APE) during the one hour collection to determine a maximum percent dose oxidized per hour (max % oxidation/h) Schneider, J. F., et al. *Clin. Chim. Acta.* 84:153–162 [1978]). Calculating the data in this manner reduced variability associated with changes in gastric emptying of the ingested dose. The quantity of $^{13}$C exhaled is estimated by assuming $CO_2$ production is 5 mmol/min/m$^2$ body surface area (Schneider, J. F., et al. *Clin. Chim. Acta.* 84:153–162 [1978]). The maximum percent dose metabolized was calculated as:

$$\text{Max \% dose/hour} = [(BSA(m^2) \times (APE_{max}/100) \times 5 \text{ mmol/min/m}^2]/0.65 \text{ mmol} \times 6$$

Where BSA is the body surface area, $APE_{max}$ is the maximum atom percent excess for a ten minute interval, 0.65 mmol is the quantity of $^{13}$C-labeled methionine administered and the constant 6 converts the 10 minute interval to one hour.

Reproducibility of the two tests were evaluated using a paired Student's t-test. In addition, a linear correlation coefficient was calculated for the two tests. The null hypothesis was that the difference between the two tests was equal to zero. The null hypothesis was tested at p<0.05.

Reproducibility results from the twenty healthy controls are given in Table 1. A paired t-test between test 1 and test 2 accepted the null hypothesis thus indicating the difference was not significantly different from zero, mean (95% CI)=−0.073 (−0.475,0.330). There was a significant correlation (r=0.945, p<0.001) between MBT test 1 and test 2. The mean of tests 1 and 2 was 6.71±2.55.

TABLE 1

MBT test 1 and 2 in healthy controls

| Subject | *Test 1 | *Test 2 | Mean (Test 1 and 2) |
|---|---|---|---|
| 1 | 6.18 | 6.01 | 6.10 |
| 2 | 13.28 | 12.81 | 13.05 |
| 3 | 5.29 | 6.14 | 5.72 |
| 4 | 7.64 | 6.44 | 7.04 |
| 5 | 4.56 | 5.21 | 4.89 |
| 6 | 4.16 | 4.47 | 4.32 |
| 7 | 6.02 | 4.72 | 5.37 |
| 8 | 13.44 | 13.87 | 13.66 |
| 9 | 5.45 | 6.88 | 6.17 |
| 10 | 7.55 | 9.00 | 8.28 |
| 11 | 6.01 | 5.82 | 5.92 |
| 12 | 4.97 | 3.87 | 4.42 |
| 13 | 6.31 | 6.33 | 6.32 |
| 14 | 7.66 | 6.93 | 7.30 |
| 15 | 5.69 | 6.34 | 6.02 |
| 16 | 8.71 | 8.72 | 8.72 |
| 17 | 5.86 | 5.98 | 5.92 |
| 18 | 5.11 | 3.98 | 4.55 |
| 19 | 4.92 | 5.62 | 5.27 |
| 20 | 4.67 | 5.78 | 5.23 |
| Mean | 6.67 | 6.75 | 6.71 |
| SD | 2.57 | 2.61 | 2.55 |
| 95% CI | 5.47–7.88 | 5.51–7.91 | 5.51–7.91 |

*Maximum percent methionine oxidation per hour.

Figure 2:
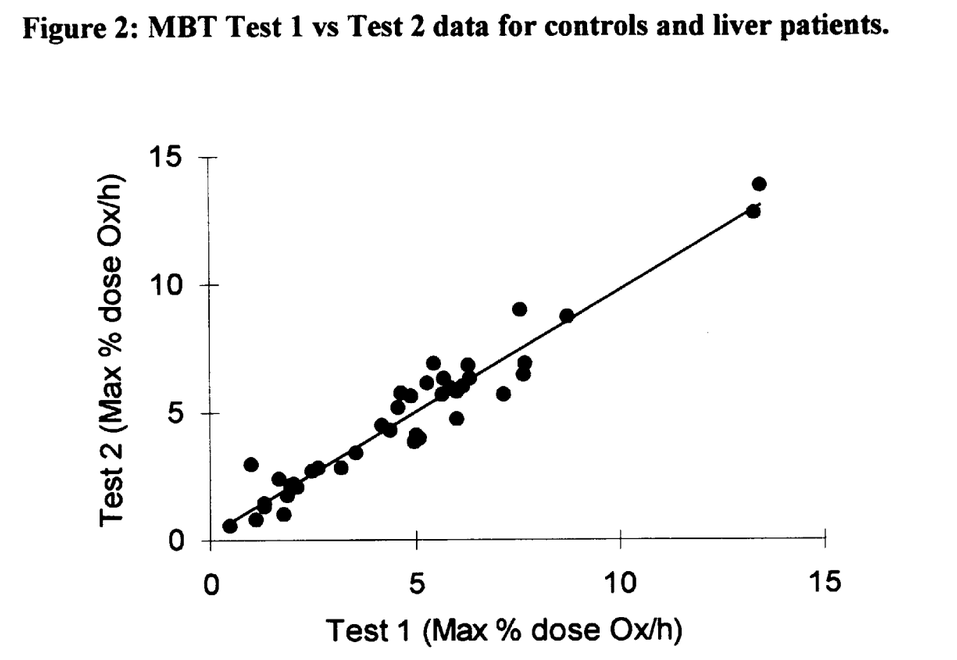
FIG. 2: MBT Test 1 vs Test 2 data for controls and liver patients.

The combined results for the MBT of healthy controls and liver patients is shown in FIG. 2. The two groups are combined to show the reproducibility was excellent in participants with or without liver disease. The correlation (r=0.97, p<0.001) reveals reproducibility of the MBT is acceptable over a broad clinical range of liver function.

Two groups are combined to show that reproducibility was excellent in patients with or without liver disease. Correlation r=0.97 P<0.001 indicates that the reproducibility of the MBT is acceptable over a broad range of liver disease in all participants.

We found that the reproducibility of the MBT was excellent in 20 volunteers as well as in the 22 patients with liver disease. Short-term reproducibility proved satisfactory as differences between test 1 and test 2 were not significantly different from zero at 95% confidence with a paired t-test. The difference between two independently administered tests was 11%. Correlation analysis yielded r=0.95 for the controls and r=0.97 for all participants.

EXAMPLE 2

Determination of the Alcohol as ASA effect on the MBT

Alcohol and ASA have a pronounced effect on mitochondria. Alcohol and ASA change the NAD/NADH ratio which decreases or increases methionine oxidation, respectively. When alcohol is metabolized to acetaldehyde, NAD is reduced to NADH and thus NAD is not available for the metabolism of $^{13}$C-methionine. Therefore, $^{13}CO_2$ production is decreased. When ASA is metabolized, NADH is oxidized to NAD making more NAD available for methionine metabolism, thus causing an increase in $^{13}CO_2$ production. This indicates that the MBT reflects $^{13}CO_2$ production. The participants were randomized to ingest either alcohol (n=9) or ASA (n=11) 15 minutes prior to the MBT. Subjects ingested 60 cc (2 oz) vodka (Smirnoff, 86 proof) dissolved in 200 ml orange juice. The protocol was then identical to that described previously in Example 1. Subjects were observed for 2 hours following alcohol administration and were driven home by a friend or family member.

The dose of ASA ingested was 30 mg/kg body weight (5–8 tablets) and was swallowed with 100 ml water, 15 minutes prior to the MBT. The protocol for breath collection was followed as described previously.

The maximum percent dose oxidized per minute was calculated for each substrate following the procedure outlined above in Example 1.

A paired Student t-test compared the mean of MBT test 1 and 2 to the MBT performed prior to the MBT performed during the ingestion of alcohol or ASA.

The mean % oxidation for all controls was 6.71±2.55. In controls who ingested alcohol the MBT decreased to 3.01±0.81 (mean change from baseline −59±17%, p<0.003) and in those who ingested ASA, the MBT increased to 8.43±1.16 (mean change from baseline 36±36%, p<0.001).

TABLE 2

Effect of alcohol and ASA ingestion on the MBT in healthy controls

| Subject | Mean T1 and T2 | Mean T1 and T2 | Alcohol | ASA |
|---------|----------------|----------------|---------|-------|
| 1 | 6.10 | | 3.36 | |
| 2 | 13.05 | | 4.54 | |
| 3 | 5.72 | | 2.76 | |
| 4 | 7.04 | | 2.22 | |
| 5 | 4.89 | | 2.97 | |
| 6 | 4.32 | | 3.39 | |
| 7 | 5.37 | | 1.86 | |
| 8 | 13.66 | | 3.52 | |
| 9 | 6.17 | | 2.45 | |
| 10 | | 8.28 | | 9.47 |
| 11 | | 5.92 | | 10.08 |
| 12 | | 4.42 | | 8.88 |
| 13 | | 6.32 | | 8.73 |
| 14 | | 7.30 | | 7.77 |
| 15 | | 6.02 | | 7.34 |
| 16 | | 8.72 | | 9.24 |
| 17 | | 5.92 | | 6.47 |
| 18 | | 4.55 | | 8.61 |
| 19 | | 5.27 | | 6.88 |
| 20 | | 5.23 | | 9.27 |
| Mean | 7.37 | 6.17 | 3.01 | 8.43 |
| SD | 3.48 | 1.41 | 0.81 | 1.16 |

Results indicated that the MBT significantly decreases with ingestion of alcohol and increases with ASA ingestion. Thus, the MBT represents changes in hepatic mitochondrial function. This example shows that the MBT is sensitive to changes in hepatic mitochondrial function introduced by xenobiotic agents and can be used as a quantitative measure of mitochondrial function.

EXAMPLE 3

Reproducibility and Correlation of the MBT with Liver Disease Severity

The objective of this example was to determine whether the MBT 1) is reproducible in patients with liver disease, 2) can distinguish healthy controls from patients with liver disease, and 3) correlates with liver disease severity as classified by Child-Pugh score.

We studied 11 patients with stable cirrhosis with no alcohol intake for >1 year, 5 actively drinking alcoholic cirrhotic patients, and 6 patients with cirrhosis and alcoholic hepatitis. Clinical characteristics, CP score and MBT results for these patients are shown in Table 3.

TABLE 3

Cirrhotic Patients with corresponding Child-Pugh score and MBT results

| Subject Number | Age | Sex | Etiology of Cirrhosis | CP Score | MBT 1 | MBT 2 | Mean |
|----------------|-----|-----|------------------------|----------|-------|-------|------|
| P1 | 44 | F | Autoimmune Hepatitis | A-5 | 5.01 | 4.09 | 4.55 |
| P2 | 26 | M | Primary Sclerosing Cholangitis | A-5 | 6.30 | 6.81 | 6.56 |
| P3 | 71 | F | Autoimmune Hepatitis | A-5 | 2.47 | 2.69 | 2.58 |
| P4 | 51 | M | Sarcoidosis | A-5 | 7.18 | 5.68 | 6.43 |
| P5 | 38 | M | Stable Alcoholic Cirrhosis | A-5 | 5.66 | 5.71 | 5.69 |
| P6 | 56 | F | Autoimmune Hepatitis | B-7 | 3.20 | 2.84 | 3.02 |
| P7 | 65 | F | Stable Alcoholic Cirrhosis | B-7 | 3.55 | 3.39 | 3.47 |
| P8 | 56 | M | Hepatitis C | B-7 | 1.67 | 2.39 | 2.03 |
| P9 | 63 | F | Stable Alcoholic Cirrhosis | B-7 | 4.36 | 4.31 | 4.34 |
| P10 | 57 | M | Stable Alcoholic Cirrhosis | B-8 | 2.63 | 2.83 | 2.73 |

TABLE 3-continued

Cirrhotic Patients with corresponding Child-Pugh score and MBT results

| Subject Number | Age | Sex | Etiology of Cirrhosis | CP Score | MBT 1 | MBT 2 | Mean |
|---|---|---|---|---|---|---|---|
| P11 | 65 | M | Hepatocellular Cancer with Hepatitis C | B-8 | 2.10 | 2.11 | 2.11 |
| P12 | 60 | M | Stable Alcoholic Cirrhosis | B-9 | 0.99 | 2.98 | 1.99 |
| P13 | 62 | M | Stable Alcoholic Cirrhosis with Hepatitis C | C-10 | 2.02 | 2.24 | 2.13 |
| P14 | 36 | M | Cirrhosis with Alcoholic Hepatitis | C-11 | 1.31 | 1.33 | 1.32 |
| P15 | 41 | F | Cirrhosis with Alcoholic Hepatitis | C-11 | 1.34 | * | 1.34 |
| P16 | 43 | F | Stable Alcoholic Cirrhosis with Hepatitis C | C-11 | 1.87 | 1.77 | 1.82 |
| P17 | 63 | M | Stable Alcoholic Cirrhosis | C-11 | 1.94 | 2.14 | 2.04 |
| P18 | 49 | F | Stable Alcoholic Cirrhosis with Hepatitis C | C-11 | 0.46 | 0.59 | 0.53 |
| P19 | 54 | M | Cirrhosis with Alcoholic Hepatitis | C-12 | 1.80 | 0.99 | 1.40 |
| P20 | 35 | F | Cirrhosis with Alcoholic Hepatitis | C-13 | 0.54 | * | 0.54 |
| P21 | 49 | M | Cirrhosis with Alcoholic Hepatitis | C-13 | 1.11 | 0.82 | 0.97 |
| P22 | 37 | F | Cirrhosis with Alcoholic Hepatitis | C-14 | 1.31 | 1.44 | 1.38 |
| Mean | 51 | | | | 2.67 | 2.86 | 2.76 |
| SD | 12 | | | | 1.90 | 1.71 | 1.79 |

*Repeat MBT test was not performed because of patient refusal.

All patients were diagnosed with cirrhosis based on characteristic clinical symptoms, standard serum liver tests, radiological testing, and/or liver histology. All patients were clinically stable.

The MBT was performed twice within 12 h as described for controls. CP classification was determined at the time of the first test and scores were calculated as shown in Table 4.

TABLE 4

Child-Pugh scoring and classification system

| Points | Prothrombin Time (seconds above control) | Albumin (g/dl) | Total Bilirubin (mg/dl) | Ascites | Encephalopathy (grade) |
|---|---|---|---|---|---|
| 1 | <4 | <3.5 | <2 | None | 0 |
| 2 | 4–6 | 3.5–2.8 | 2–3 | Mild | 1–2 |
| 3 | >6 | <2.8 | >3 | Moderate/Severe | 3–4 |

| CP Classification | CP Score (total Points) |
|---|---|
| A | 5–6 |
| B | 7–9 |
| C | 10–15 |

For example, a patient with a prothrombin time of <4 seconds above normal, albumin of 3.0 g/dl, total bilirubin of 2.2 mg/dl, ascites (mild), and no encephalopathy would accumulate a score of 8 and would be classified Child-Pugh class B (CP-B). The correlation between CP classification and MBT values in patients was determined. Mean MBT values and 95% confidence intervals were compared for controls and liver patients.

Figure 3:
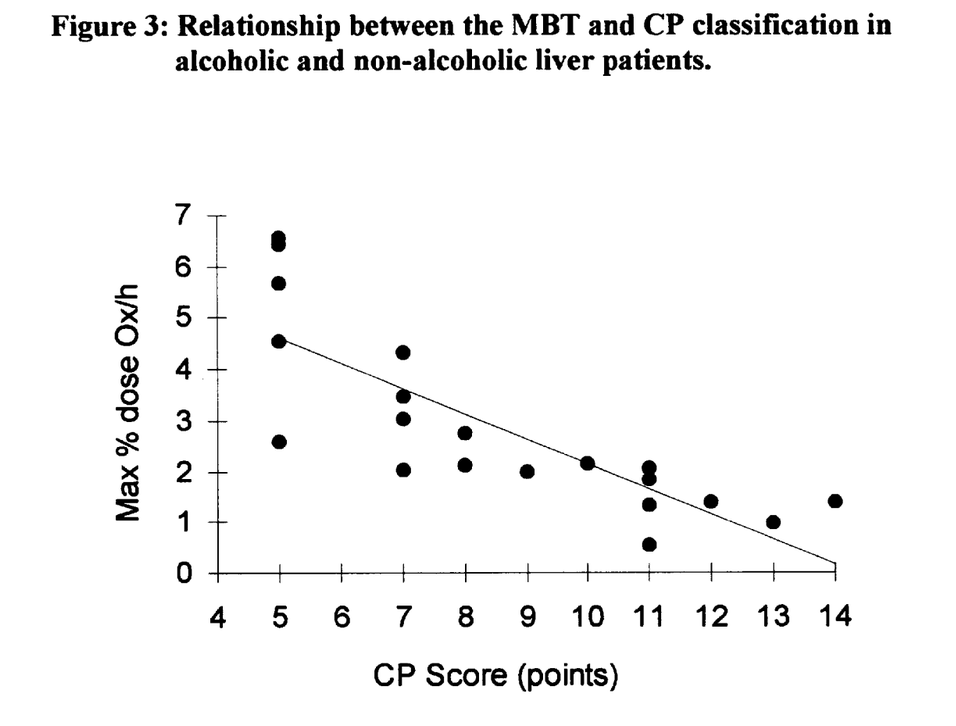
FIG. 3: MBT vs CP score.

A plot of the MBT results with corresponding CP score is given in FIG. 3. The correlation for this data was highly significant (r=−0.81, p<0.001). This indicates that the MBT correlates with liver disease severity as classified by the CP scores. A one-way statistical analysis of variance (ANOVA) indicated the MBT values (mean±SD) 5.16±1.61, 2.81±0.94, and 1.45±0.55 for CP scores A, B, and C respectively, were significantly different (p<0.001). Thus, the MBT distinguished patients with different liver disease severity. MBT results for the control subjects and all patients were 6.71 and 2.85 respectively. The 95% confidence intervals did not overlap, thus indicating the MBT detected a statistically significant difference between these two populations. Correlation of reproducibility in liver patients (r=0.93) was comparable to that of controls (r=0.95).

Using the threshold of 4% (maximum % oxidized/h) patients were classified as either having normal or abnormal mitochondrial function. Abnormal function was classified as an MBT<4% and normal function of >4%. Utilizing the threshold of 4%, sensitivity was 94%, specificity 96%, and accuracy 95% (see Table 5).

TABLE 5

Sensitivity and Specificity for all study participants

| MBT (%) | CP B/C | Controls/CP A |
|---|---|---|
| <4.0 | 16 Total Positives | 1 False Positive |
| ≧4.0 | 1 False Negative | 24 True Negatives |

The sensitivity, specificity, and accuracy of the test were calculated as follows:

Sensitivity=No. of True Positives/Total with Disorder= 16/17×100=93%

Specificity=No. of True Negatives/Total free of Disorder= 24/25×100=96%

Accuracy=True Positives+True Negatives/Total Investigated=40/42×100=95%

The MBT was able to distinguish healthy controls and CP A from CP B/C patients with high specificity and sensitivity. There was no significant difference between controls and CPA. This may be due to the small number of CP A patients in the study or that this group of cirrhotic patients have not lost significant function. Our data suggests that as liver disease progresses either through the CP scoring system or from stable cirrhosis to alcoholic hepatitis, mitochondrial function is compromised. Patients with CP B/C have the poorest survival and thus need to be distinguished from healthy controls and CP A.

The data indicates the MBT has clinical utility in distinguishing patients with normal function from those with abnormal function despite presence of cirrhosis. In addition, serial testing of patients over time may prognostically indicate progression of liver disease and provide information for optimal timing of therapeutic measures including liver transplantation. Furthermore, serial testing may indicate a response to treatment and therefore allow the clinician to employ a cost effective treatment strategy by either continuing useful therapy or discontinuing ineffective therapy.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of assessing hepatic mitochondrial function in a subject comprising the steps of:
   a) administering to said subject an effective amount carbon-labeled methionine metabolite to said suet;
   b) collecting expired breath from said subject; and
   c) measuring the amount of labeled carbon in said expired breath to assess hepatic mitochondrial function in said subject.

2. The method according to claim 1 wherein said carbon-labeled methionine metabolite is selected from the group consisting of $^{13}C$ methionine metabolite, $^{13}C$ methionine metabolite, a mixtures thereof.

3. The method according to claim 1 where in said carbon-labeled methionine metabolite is labeled at the 1-position of the methionine metabolite.

4. The method of claim 1 wherein said carbon-labeled methionine metabolite comprises a plurality of labeled carbons.

5. The method according to claim 1 wherein said labeled carbon in said expired breath is labeled carbon dioxide.

6. The method according to claim 5 wherein said labeled carbon dioxide is $^{13}C$ carbon dioxide.

7. The method according to claim 1 wherein said administering step comprises administering carbon-labeled methionine metabolite in a pharmaceutically acceptable carrier.

8. The method according to claim 1 further comprising comparing said amount of expired labeled carbon with a standard, whereby said comparing yields a measure of hepatic mitochondrial function.

9. The method according to claim 8 wherein said standard comprises the mean value of expired label in a control population without hepatic disease or hepatic dysfunction.

10. The method according to claim 1 or claim 8 wherein said assessing mitochondrial function is used to diagnose hepatic disease or hepatic dysfunction.

11. The method according to claim 10 wherein said hepatic disease or dysfunction is selected from the group consisting of chronic liver disease, fulminant hepatic failure, viral-induced liver disease, metabolic liver disease, and hepatic dysfunction associated with sepsis or liver trauma.

12. The method according to claim 1 wherein said measuring comprises isotopic measurement of labeled carbon.

13. The method according to claim 12 wherein said measurement is selected from the group consisting of mass spectrometric measurement, laser measurement, infrared detection, nuclear magnetic resonance and liquid scintillation counting of labeled carbon.

14. The method of claim 1 wherein said carbon-labeled methionine metabolite is selected from the group consisting of carbon-labeled S-adenosylmethionine, S-adenosylhomocysteine, homocysteine, cystathionine, homoserine and α-ketobutyrate.

15. The method of claim 14, wherein said carbon-labeled methionine metabolite is carbon-labeled S-adenosylmethionine.

16. The method of claim 14, wherein said carbon-labeled methionine metabolite is carbon-labeled S-adenosylhomocysteine.

17. The method of claim 14, wherein said carbon-labeled methionine metabolite is carbon-labeled homocysteine.

18. The method of claim 14, wherein said carbon-labeled methionine metabolite is carbon-labeled cystathionine.

19. The method of claim 14, wherein said carbon-labeled methionine metabolite is carbon-labeled homoserine.

20. The method of claim 14, wherein said carbon-labeled methionine metabolite is carbon-labeled α-ketobutyrate.

21. The method of claim 20, wherein said step of administering is performed orally.

22. The method of claim 1, wherein said step of administering is performed orally.

23. The method of claim 1, wherein said step of administering is performed intravenously.

24. The method of claim 1, wherein said step of administering is administering to said subject an effective amount of a mixture of carbon-labeled methionine metabolite and carbon-labeled methionine to said subject.

* * * * *

UNITED STATES PATENT AND TRADEMARK OFFICE
CERTIFICATE OF CORRECTION

PATENT NO: 5,961,470

DATED: October 5, 1999

INVENTOR(S): David A. Wagner, Graham M. Woolf

It is certified that errors appear in the above-identified patent and that said Letters Patent is hereby corrected as shown below:

Col. 11, claim 1, line 26, after "amount", insert --of--.

Col. 11, claim 1, line 27, delete "suet", and insert --subject--.

Col. 11, claim 1, line 35, delete "a", and insert --and--.

Signed and Sealed this

Sixth Day of June, 2000

Attest:

Q. TODD DICKINSON

Attesting Officer

Director of Patents and Trademarks